United States Patent [19]
Pepin

[11] Patent Number: 5,652,056
[45] Date of Patent: Jul. 29, 1997

[54] HYDROXYAPATITE FILAMENT

[76] Inventor: John N. Pepin, P.O. Box 143, Greenville, Me. 04441

[21] Appl. No.: 709,440

[22] Filed: Aug. 20, 1996

Related U.S. Application Data

[60] Provisional application No. 60/002,807, Aug. 25, 1995.
[51] Int. Cl.$^6$ .......................... D02G 3/00; C01B 15/16
[52] U.S. Cl. ..................... 428/364; 428/372; 423/308; 423/309; 423/311
[58] Field of Search .................. 428/364, 372; 423/308, 309, 311; 501/95; 206/35

[56] References Cited

U.S. PATENT DOCUMENTS

| | | | |
|---|---|---|---|
| 4,503,157 | 3/1985 | Hatahira | 423/308 |
| 4,880,610 | 11/1989 | Constantz | 423/309 |
| 4,968,317 | 11/1990 | Tormala et al. | 606/77 |
| 5,227,147 | 7/1993 | Yoshimura et al. | 428/311 |

OTHER PUBLICATIONS

Yoshimura et al, Processing and Mechanical Properties of Hydroxyapatite (HAP) reinforced with HAP Whiskers; 1996, pp. 1715–1723.

*Primary Examiner*—Newton Edwards

[57] ABSTRACT

A substantially pure hydroxyapatite filament provides the reinforcement for composite materials used for bone replacement and repair. Its biocompatibility and high strength reveal opportunities for strong, tough and biocompatible composites to replace diseased, fractured or missing areas of bone. One such opportunity is a hydroxyapatite fiber reinforced hydroxyapatite matrix composite. This composite has higher strength and toughness than sintered hydroxyapatite yet has excellent biocompatibilty and mechanical properties which can be tailored to mimic replaced bone. Methods for filament fabrication include low temperature extrusion of a precursor gel filament reinforced with hydroxyapatite whiskers, high temperature sinter-extrusion and high temperature glass filament formation followed by reconversion to hydroxyapatite by intermediate temperature heat treatment.

4 Claims, 5 Drawing Sheets

HYDROXYAPATITE FILAMENT

This invention was made with government support under grant number R3AR43915A awarded by the National Institutes of Health. The government has certain rights in this invention.

BACKGROUND OF THE INVENTION

This application claims the benefit of U.S. provisional application number 60/002,807 filed on Aug. 25, 1995, now abandoned.

2. Field of the Invention

This invention resides in the field of orthopedic and dental biomaterials and it specifically relates to materials and structures designed to replace missing or diseased areas of bone.

3. Prior Art

Calcium phosphate based materials such as hydroxyapatite and $\alpha$ and $\beta$ tricalcium phosphate have been used as bone replacement materials in dental and orthopedic applications. These materials are completely biocompatible. Their bioresorbability or the rate at which they degrade and become absorbed when implanted into the body is dependent on constituent composition, crystal structure and porosity. The mineral content of bones and teeth is primarily hydroxyapatite. Hydroxyapatite is a crystalline material with the chemical formula $Ca_{10}(PO_4)_6(OH)_2$ having the Ca/P molar ratio of 1.67. Living host bone will form chemical bonds to hydroxyapatite so it has received a great deal of attention for bone replacement applications. Its synthetic form is often used to fill defects or build bone areas by allowing bone ingrowth into implanted hydroxyapatite particles and slurries. In dental applications it has been used to build up the alveolar ridge and fill areas of non-structural missing bone. Hydroxyapatite sintered from a microcrystalline powder has been used for small implants with low mechanical loading such as small bone implants for the ear. In still another application, plasma sprayed hydroxyapatite is used to coat titanium hip implants for better fixation at their interface with the femur. Thus far, however, sintered hydroxyapatite has not been used for high load bearing applications with complex stress states such as joint replacement prostheses because its current forms do not have the necessary strength and toughness to support high cyclic loads especially in tension and shear. It is also brittle and hence its strength is sensitive to internal and surface flaws.

In bone replacement applications where high strength and toughness is required, metals or combinations of metals, ceramics, and high density plastics are used. Joint replacement prostheses, for example, are fabricated from cobalt chrome alloys, titanium, stainless steel, monolithic ceramics or other relatively inert material. While they initially have sufficient strength, these materials have moduli or stiffnesses which are an order of magnitude higher than the bone they are replacing. They are also mechanically isotropic, that is, they have the same properties in all directions within the material. Bone is a low modulus, anisotropic composite material whose reinforcement is tailored to support the loads it experiences. When bone is replaced with these high modulus materials the interfacing host bone tissues are shielded from experiencing naturally occurring stress distributions. This stress shielding causes living bone tissue to resorb or become weaker and less dense. This further complicates fixation of the implant for long periods.

In joint replacement applications metal components often form a bearing surface with a plastic component on the opposite side of the joint. Wear at this bearing surface releases particles which can cause inflammatory reactions in the surrounding tissue. These problems and the continued cyclic load environment limit the long term effectiveness of the joint replacement. Hence these joint replacements are usually performed only on older patients. Joint replacement surgery in younger patients must typically be repeated after a period of time to repair damaged tissues and replace components. These added surgeries are usually higher risk and more difficult to perform.

Several U.S. patents describe applications of hydroxyapatite, mainly as a coating material for strong substrate materials. Coating methods are described in U.S. Pat. Nos. 5,279,831, 5,188,670, 5,128,169, and others. The incentive to use hydroxyapatite coatings is that the hydroxyapatite enhances the growth of dense bone in its neighborhood and further that it bonds chemically to this new bone tissue. Coating a structural material with hydroxyapatite takes advantage of these positive characteristics even though the hydroxyapatite itself, in prior art forms, does not have the strength or toughness to be used as the load bearing structure of an implant. Coatings, however, are typically very thin interfaces which are subject to flaking, chipping and the like. In addition, they only provide a two-dimensional interface upon which bone can attach limiting the strength and toughness of this attachment.

Tagai, et al in U.S. Pat. Nos. 4,735,857 and 4,820,573 describe a calcium phosphate glass fiber with a Ca/P molar ratio between 0.2 and 0.6. The use of this fiber in a cotton-like staple form or cloth form is described as a bone defect filler to encourage bone growth into the defect; however, the patents do not reveal the fiber's tensile strength or rate of resorption after implantation. A similar cotton-like product is described by Fuji in U.S. Pat. No. 4,659,617. These fiber forms may be useful in bone filling applications but in many cases the removal of diseased bone or repair of broken bones requires fixation with structures which are strong, tough and completely biocompatible. Unlike pure crystalline hydroxyapatite which has been shown to be totally biocompatible, these prior art glass fibers are comprised of mixtures of several different materials at least in part to aid in processing into fiber. These mixtures will have varying biocompatibility, resorption, and strength and hence their application to long term bone replacement components supporting high mechanical loads will be limited.

OBJECTS AND ADVANTAGES

It is the object of this invention to provide a high strength hydroxyapatite filament as a mechanical building block for a class of strong, tough biomaterials. More particularly, the objects and advantages of the present invention are:

(a) to provide strong hydroxyapatite filaments to reinforce a hydroxyapatite matrix material resulting in a composite material which displays excellent biocompatibility and durability when implanted as a bone replacement component or prosthesis. The mechanical properties of this composite material can be tailored to mimic the mechanical properties of the replaced bone thereby eliminating the stress shielding which occurs with currently used high modulus materials. This composite will also exhibit the necessary toughness and strength to support high mechanical loads in the area of the replaced bone. When implanted, sintered hydroxyapatite has a very high ability to enhance formation of dense, new bone around it and it has a very low rate of resorption. Unlike prior art materials, the hydroxyapatite fiber reinforced hydroxyapatite matrix composite will be stable for long periods of time when implanted and, if wear particles are released from this composite, they will not cause the inflammatory response of the metals, ceramics and plastics currently used. The active fiber interface between this composite and the living bone tissue can be woven such that voids between filament bundles allow bone ingrowth to provide lifelong fixation of an implant. Mechanically and biologically, this composite will be as close to living bone tissue as possible.

(b) to provide strong hydroxyapatite filaments in woven two-dimensional, three-dimensional, and multi-dimensional reinforced shapes which act as scaffolds for bone ingrowth while preserving needed strength during the bone growth process. A specific application for a hydroxyapatite fabric would be a dam to prevent the growth of epithelial cells into a hydroxyapatite slurry injected below the gum line to build up the bone structures supporting teeth. The current practice uses a rubber dam to block epithelial cell growth into the implanted slurry to give bone the time to grow into the slurry. This rubber dam has to be removed surgically whereas a hydroxyapatite fabric dam could remain in place. The hydroxyapatite fabric dam would therefore eliminate this additional surgery with its cost, lost time and discomfort to the patient.

(c) to provide significant improvements in fixation of current metal implants by weaving hydroxyapatite filaments into the metal implant surface yielding a strong, three-dimensional interface for bone ingrowth. This three-dimensional interface will be formed by hydroxyapatite filament loops extending outward from the metal surface. Prior art methods use a hydroxyapatite coating which can break off, chip or flake reducing the bone-implant interface strength and causing loosening of the implant.

It is a further object of the invention to provide a hydroxyapatite fiber reinforced composite material whose matrix is designed to resorb in a controlled manner. This will allow living tissue to grow into the implant to anchor it or perhaps eventually completely replace the matrix of a fiber reinforced composite implant. The living bone tissue is then capable of growth and remodeling to suit changing mechanical and physiological conditions. A gradient in the rate of resorption and hence rate of living bone intrusion into the matrix might also be provided by using several matrix materials having different rates of resorption. These materials could be deposited in layers from the inside of the implanted composite to its outer, bone-interface surface.

SUMMARY

In summary, bone replacement materials currently being used to replace highly loaded areas of bone like joint replacements are not well suited for this task because of their high stiffness and lack of complete biocompatibility. This invention starts with the most biocompatible material available, hydroxyapatite, and provides a strong form of this material, a filament. This filament can then be used to build an entire set of bone replacement materials and structures. These materials and structures will provide lifetime bone replacement components used in dental, maxillofacial and orthopedic reconstruction.

DESCRIPTION OF THE INVENTION

Figure 1:
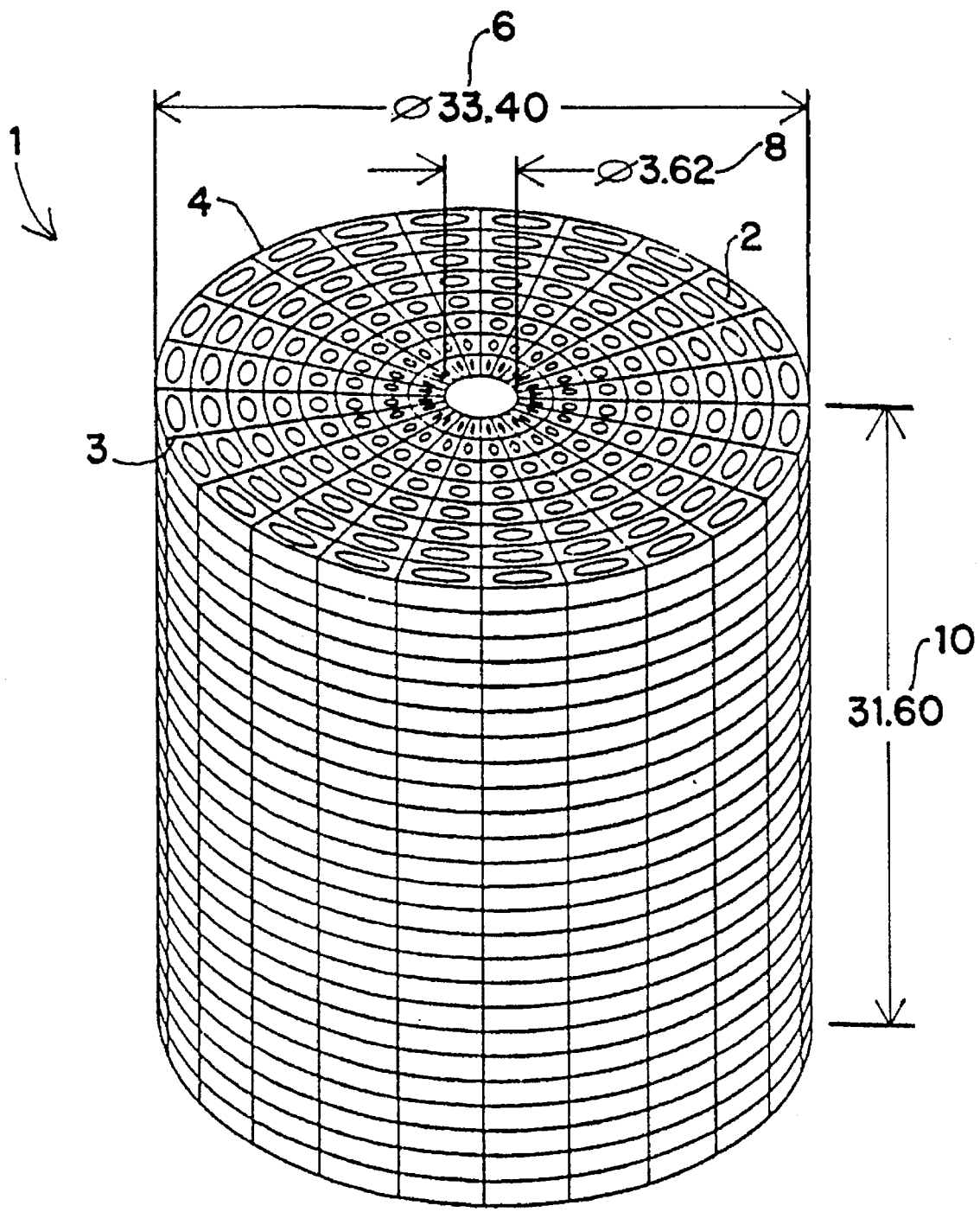
FIG. 1 is a schematic of a three dimensionally woven cylinder.
Figure 2:
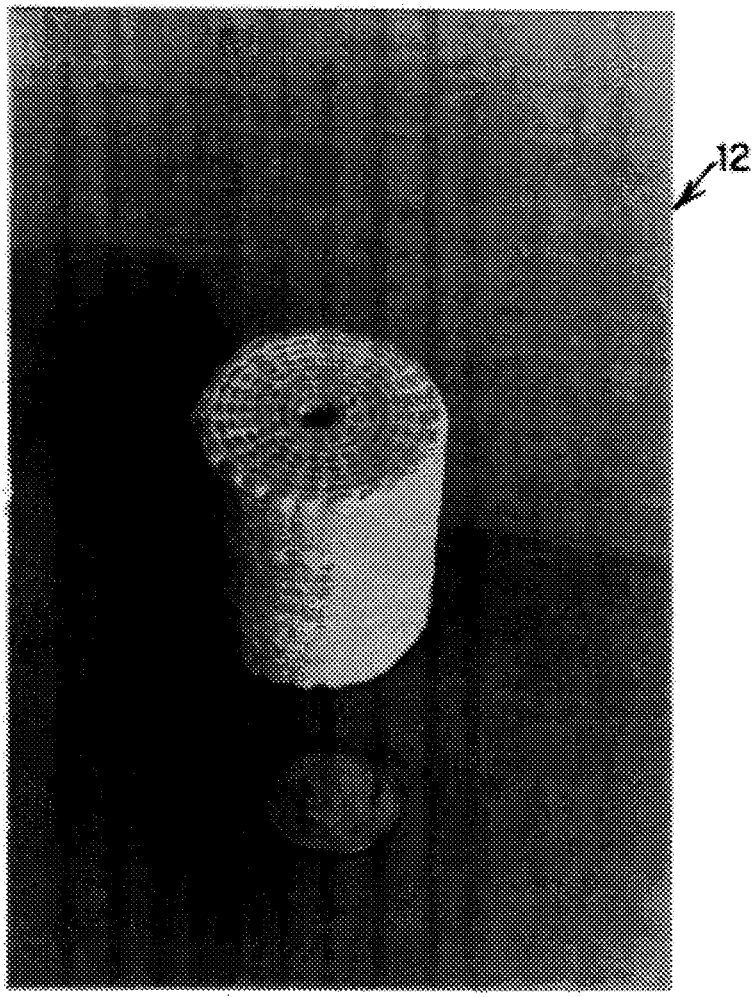
FIG. 2 shows a three dimensionally woven silica fiber reinforced silica composite cylinder.

The invention is a hydroxyapatite filament and applications of the filament useful in bone replacement and repair. One such useful form is shown in FIG. 1. FIG. 1 shows a schematic of a cylinder 1 which is comprised of interwoven axial 2, radial 3, and circumferential 4 fiber bundles. Typical inside diameter 8, outside diameter 6 and length 10 dimensions are given in millimeters. Diameter dimensions are typical of those which might be required in replacing a section of long, highly loaded area of bone. In another embodiment, orientation of fiber bundles can be changed to suit a particular loading requirement of a bone section to be replaced. For example, to give cylinder 1 higher torsional stiffness, fiber bundles 2 currently shown in the axial direction could be oriented at an angle relative to the cylinder axis. The technology exists to weave these orthogonally reinforced cylinders. FIG. 2 shows a silica fiber reinforced silica matrix cylinder 12 whose dimensions approximate the values given for cylinder 1. The preform or woven fiber network of this cylinder can be obtained from Techniweave, Inc. in Rochester, N.H., U.S.A.

The technology to weave such a cylinder was developed by the aerospace industry. Multidirectionally woven filament bundles, or preforms, are the reinforcing skeletons for silica fiber reinforced silica antenna windows and carbon fiber reinforced carbon missile nosetips and rocket nozzles. These combinations of fiber and matrix are instructive since high strength fibers combine with brittle matrices to yield composites which are strong, tough, and damage tolerant. For example, a steel nail can be hammered through a multidirectionally reinforced carbon-carbon composite—a composite material with a brittle fiber reinforcing a brittle matrix. This characteristic is due to the network of microcracks in the composite allowing multiple failure paths and local yielding of the composite material in the area of high stresses. The aerospace industry is clearly distinct from the field of the invention and the constituent fibers and matrices of these aerospace composites do not have the biocompatibility and bone growth enhancing features of hydroxyapatite. However, if combined with a strong hydroxyapatite filament, the multidirectional weaving technology could be useful to fabricate woven shapes whose mechanical properties mimic those of replaced bone. Bone itself is a composite material with complex reinforcement orientations within it and the better the mechanical property simulation of replaced bone tissue, the better a bone replacement implant will perform.

Three-dimensional woven shapes, two-dimensional woven fabrics, chopped fiber mats, and random fiber felts are all examples of fiber forms which can be combined with a matrix to yield a composite material for bone replacement and repair. One combination of constituent fiber and matrix which would result in an excellent bone replacement material is hydroxyapatite fiber reinforced hydroxyapatite. Such a composite with a strong hydroxyapatite fiber reinforcing a brittle hydroxyapatite matrix would yield a strong, tough, biocompatible, and mechanically tailorable bone replacement material. The hydroxyapatite filament reinforcement of these composites could be random or oriented and the composite could have either continuous or discontinuous hydroxyapatite filaments. Another embodiment would use the same hydroxyapatite fiber but a different matrix such as tricalcium phosphate, collagen, or polymerizable proteins. These would have controlled resorption so that living host bone would grow into the fiber shape as the matrix resorbs and recedes from the bone/implant interface.

Unimpregnated preforms or free standing continuous filament woven shapes without any matrix have sufficient strength and post-weaving formability to be useful as a scaffold for bone ingrowth. Unlike the prior art cotton-like bone filling fibers, however, these preforms would provide significant mechanical integrity to a weakened area before and during the bone ingrowth and healing process. Bundles of hydroxyapatite filaments woven into these three-dimensional shapes would provide excellent biocompatibility, controlled porosity and mechanical strength. Bundle sizes in the woven shape could be in the range of 3000 to 12000 hydroxyapatite filaments.

What is needed to take advantage of this composite technology for bone replacement applications is a strong hydroxyapatite filament to provide the reinforcement. Filament diameters useful for the reinforcing applications mentioned are between 5 and 100 microns. A tensile strength in excess of 140 MPa would be useful but preferably the tensile strength should be above 300 MPa. The modulus of the fiber need not be high since bone itself has a rather low modulus. A modulus range of 40–500 GPa would be acceptable with the preferable range of 80–200 GPa.

Three methods are given for fabricating such a hydroxyapatite filament.

Method 1

Figure 3:
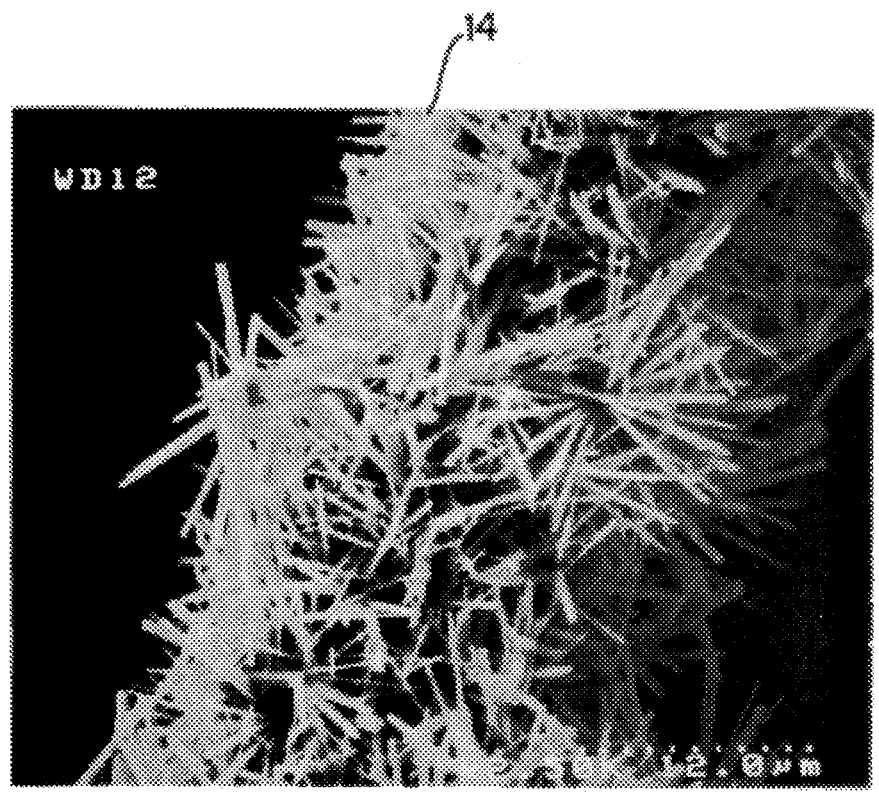
FIG. 3 shows hydroxyapatite whiskers.

The first method uses hydroxyapatite whiskers 14 shown in FIG. 3. Whiskers of other materials such as silicon carbide are routinely used to reinforce ceramics, metals, and plastics due to their high strength. Hydroxyapatite whiskers are needle-like crystals of hydroxyapatite. They are typically 8–20 microns long and the largest lateral dimension is less than 1 micron. Whiskers 14 are precipitated and grow like flowers in a solution. The hydroxyapatite whiskers are used to reinforce a hydroxyapatite filament along the axis of the filament giving the filament preferential strength along its axis.

The process to make the whiskers uses a solution of calcium-ethylenediaminetetraacetic acid (EDTA) chelate and phosphoric acid. This process is given as follows:

1. Make 250 ml of a 0.1 molar Calcium EDTA solution by combining 7.31 g of EDTA and 2.50 g of $CaCO_3$ with 200 ml of deionized water. Adjust the solution pH with $NH_4OH$ until the solids dissolve. Final solution pH should be 7. Fill to the volumetric flask line with deionized water.

2. Make 100 ml of 0.3 molar $H_3PO_4$ by placing 3.46 g $H_3PO_4$ (85%) in a 100 ml volumetric flask. Fill the flask to the line with deionized water.

3. Mix 5 ml of Ca EDTA solution with 5 ml of the phosphoric acid solution and adjust the solution pH to 7. This requires the addition of $NH_4OH$ which increases the volume by about 1 ml.

4. Place the solution in a stainless steel tube whose volume is twice the volume of the solution, seal the tube, and heat to 250° C. for 1 hour. Quench the tube in a water bath to reduce the temperature very rapidly and remove the liquid/whisker mixture inside by pouting it into a beaker. Flush the tube with deionized water to wash whiskers along the walls of the tube into the beaker. Allow the whiskers to settle to the bottom of the beaker and pour off the liquid until most is removed. Wash the whiskers with deionized water repeatedly until clean and store in the beaker under the water until ready for use in the process. The chelate reagent can also be recovered from the decanted solution.

The reaction occurs by thermal dissociation of $Ca(EDTA)^{2-}$ according to the following equations:

$$Ca(EDTA)^{2-} \rightarrow Ca^{2+} + EDTA^{4-} \tag{1}$$

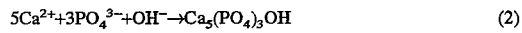
$$5Ca^{2+} + 3PO_4^{3-} + OH^- \rightarrow Ca_5(PO_4)_3OH \tag{2}$$

There are occupational health issues associated with the manufacture and handling of whiskers if they become airborne. Hydroxyapatite whiskers should either be in a fluid medium or encapsulated in a matrix at all times. Once encapsulated the whiskers pose no problem even if the composite is machined. Resulting dust particles do not have the whisker shape and are handled in routine ways. Silicon carbide whiskers are similar in size to hydroxyapatite whiskers and guidelines for handling these are given in ASTM E 1437-91.

The next step in this method 1 process is to break the whiskers off their "flowers" so that they can be suspended as individual whiskers in a liquid medium such as water or alcohol. This is done by ball milling the whiskers with plastic balls. If ceramic media are used to mill the whiskers the ceramic media will grind the whiskers into powder. The plastic balls will break the whiskers off the "flowers" and allow them to be suspended in the water. Fill a small plastic bottle halfway with 6.33 mm diameter plastic balls such as Delrin balls available from Hoover Precision Products in Sault Ste. Marie, Mich. Fill the remainder of the bottle with the whisker and water mixture and place on a jar mill for 3 hrs. Remove the mixture and separate from the balls by washing with deionized water. Store the whiskers in the deionized water.

The next step is the formation of a precursor gel filament with whiskers imbedded in it. To make this precursor filament from the mixture of water and whiskers, ammonium alginate is added to this mixture to thicken it and form the gel filament. The ammonium alginate can be obtained from Kelco, a division of Merck & Co., in San Diego. This mixture is then extruded through a small orifice, approximately 0.3 mm in diameter, into a dilute acid such as 0.3M phosphoric acid. The process of extrusion through an orifice aligns the whiskers with the direction of fluid flow. The ammonium alginate then gels as soon as it is exposed to the acid effectively freezing the whisker alignment in the gel fiber.

The hydroxyapatite filament is formed by drying the gel fiber for 24 hrs at room temperature and then heat treating it in air at 1100°–1200° C. for three hours. The ammonium alginate gel oxidizes completely leaving no ash residue in the hydroxyapatite filament.

In another embodiment of this method the whiskers are mixed with a microcrystalline hydroxyapatite powder before the ammonium alginate is added. The powder eventually acts to bind the whiskers together in the filament. The volume fraction of whiskers-to-powder can range from 3 volume percent to 60 volume percent. When whiskers and powder are mixed, the powder particle diameter must be smaller than the typical whisker cross section. Otherwise, the process is like trying to mix pencils with basketballs. A small powder particle size prevents separation of the powder from the whiskers during mixing and ensures high density packing of whiskers within the powder. Also, it will allow the laminar flow of the fluid medium to orient the whiskers more easily during extrusion of the alginate mixture. Most of the particles of a sinterable hydroxyapatite powder are less than 60 microns in size. These particles are made up of loosely agglomerated microcrystals about 0.01 microns in size. When milled in deionized water these particles break up easily to form a colloidal suspension. The whiskers are mixed into this suspension with a ball mill or mixer. Finally, the ammonium alginate is added and mixed. A suitable microcrystalline hydroxyapatite powder is available from CAM Implants in Leiden, The Netherlands.

Figure 4:
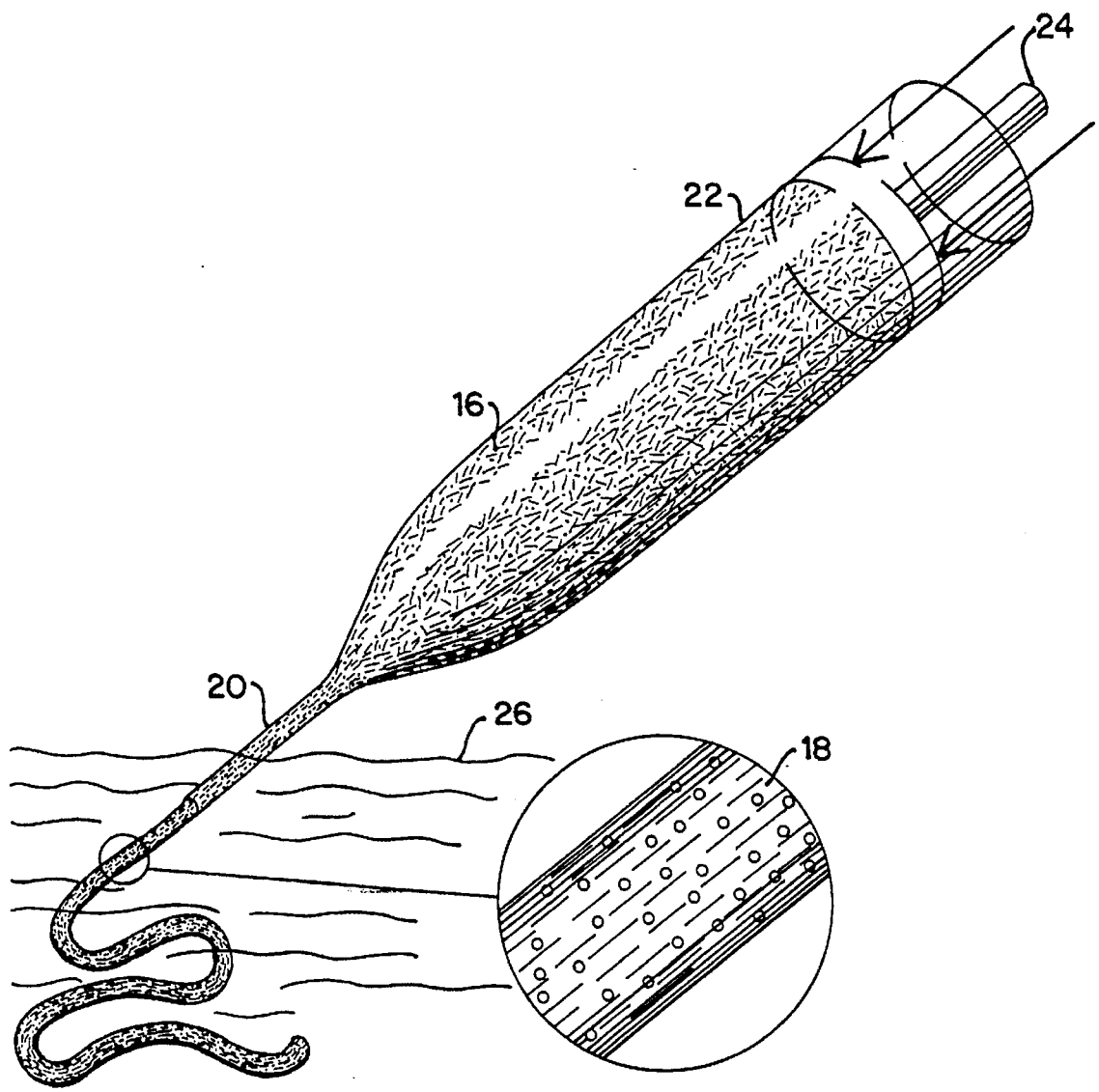
FIG. 4 shows a piston and cylinder extruding a gel containing hydroxyapatite into a dilute acid bath to form a precursor fiber.

The extrusion of this mixture is the same as discussed previously for forming the gel fiber with whiskers only. The process is shown in FIG. 4. A mixture of water, ammonium alginate, hydroxyapatite whiskers, and hydroxyapatite powder 16 is placed in tube 22. Piston 24 pushes the mixture through a necked down region 20 in the glass tube. The ammonium alginate in the mixture gels as soon as it is exposed to acid 26. Gel fiber 18 is thus formed.

The gel fiber is then dried once again at room temperature for 24 hours and heated to the sintering temperature of hydroxyapatite—between 1100° and 1200° C. The hydroxyapatite whisker reinforced hydroxyapatite filament is formed as the ammonium alginate oxidizes and the powder and whiskers sinter.

Another variation of method 1 extrudes the mixture onto a porous surface allowing the liquid medium to be sucked away leaving the whisker or whisker/powder combination at the surface. Glycerine can be substituted for water as the solvent for this variation. This process densities or consolidates the solid constituents of the mixture before heat treatment. Suitable porous media include membranes available from Millipore Corporation in Bedford, Mass.

Method 2

Figure 5:
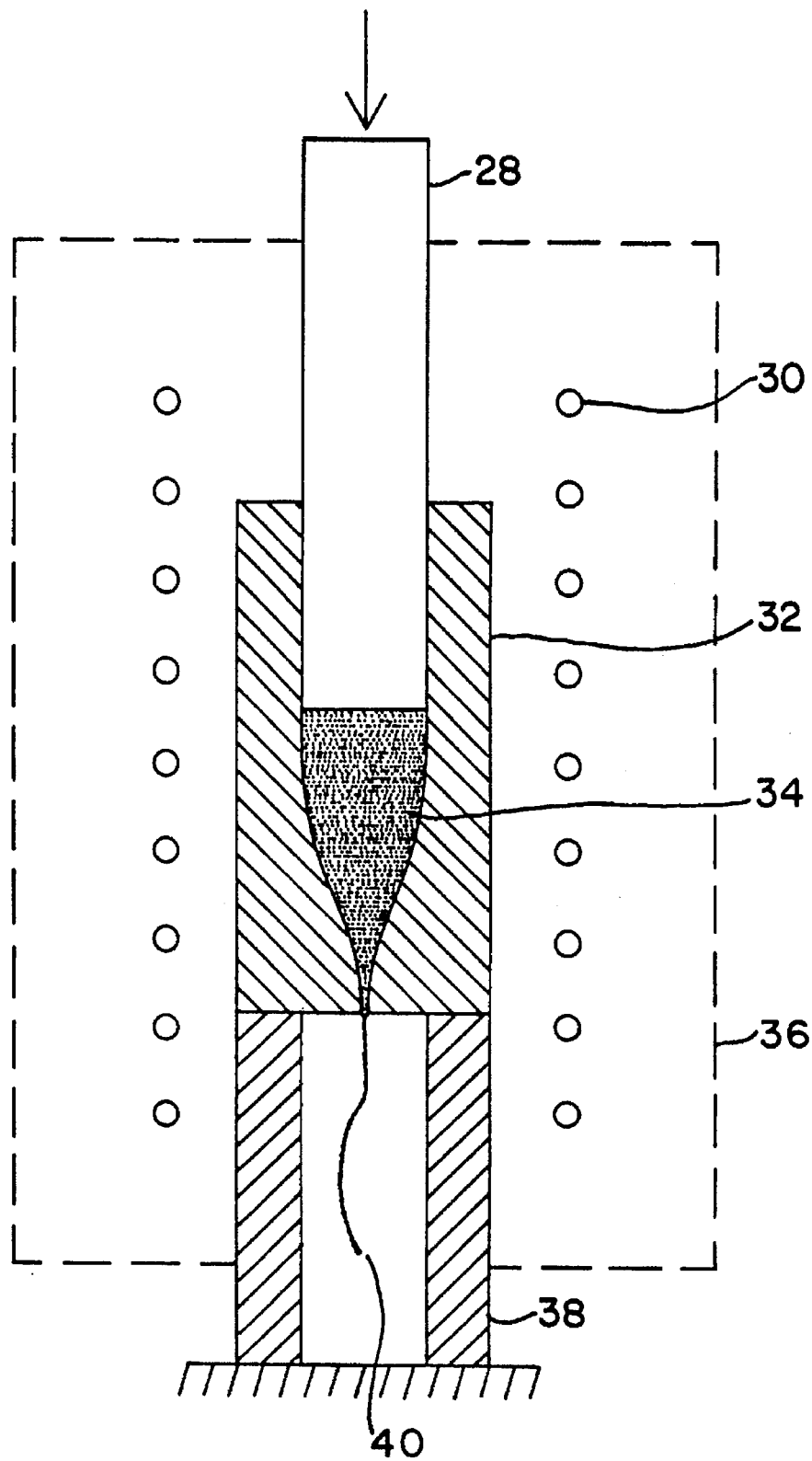
FIG. 5 shows a furnace and die arrangement extruding a hydroxyapatite filament at high temperature.

Method 2 is a high temperature sinter-extrusion process. The microcrystalline hydroxyapatite powder or powder/whisker mixture is heated to the sintering temperature of 1200° C. and forced through an orifice to create the filament. FIG. 5 shows a schematic of this method. Powder mixture 34 is surrounded by die 32 which is supported by base 38. Furnace coils 30 contained within furnace boundary 36 heat the assembly to the desired temperature. At the sintering temperature a piston 28 pushes downward on the powder mixture forcing it through an orifice to form filament 40.

In a process called sinter-forging, known in the art, hydroxyapatite powder can be deformed under high pressure at its sintering temperature. High temperature extrusion of submicron diameter ceramic powders has also been done using area ratios of piston-to-extruded shape of 5 to 10. High temperature extrusion is aided if the hydroxyapatite powder has submicron diameter particles and a small amount of additive such as a glass is used as a lubricant at the sintering temperature.

Method 3

Method 3 forms the hydroxyapatite filament in much the same way glass filaments are formed commercially. The hydroxyapatite powder is heated to a temperature in excess of 1400° C. until it forms a glass in a viscosity range which can be pulled through one or more orifices and cooled. The furnace arrangement is similar to FIG. 5. The range of orifice sizes for this method is 0.5–3 mm in diameter. As the molten glass filament is pulled through each orifice it forms a meniscus or necks down to a diameter between the desired 5–100 microns. It is cooled rapidly, a coating or sizing is added to protect the filament surfaces and the filaments are then wound on a take up spool. This process is well known in the art. At this point, however, the filament is no longer the crystalline hydroxyapatite, having lost its crystalline structure and its hydroxyl (OH) groups during the high temperature processing. The filament is a metaphosphate glass. This glass filament can then be reconverted to a hydroxyapatite filament by heat treating it in air at 600° C. for 1 to 3 hours.

A variation of method 3 includes formation of the glass filament by means other than extrusion through a hole. These means include dropping the glass onto a spinning disk or blowing air into a molten glass pool to fiberize the glass. These methods, also known in the art, would provide the glass filament precursor to the hydroxyapatite filament.

CONCLUSION, RAMIFICATIONS AND SCOPE OF THE INVENTION

Thus the hydroxyapatite filament of the current invention provides a biocompatible building block from which many materials for bone replacement and repair are possible. As a reinforcement fiber for composite bone replacement implants it provides the needed toughness and strength. Due to its high temperature stability and inertness it can be processed with many matrix materials. These matrix materials may be stable in vivo, resorb in a controlled manner, provide timed release of medication, or provide other necessary functions. Bundles, yards or tows of hydroxyapatite filaments woven into two-dimensional, three dimensional, or multidimensional forms can provide a stable scaffold for bone ingrowth while retaining tailored mechanical properties while the ingrowth occurs.

While my above description contains many specificities, these should not be construed as limitations on the scope of the invention, but rather as an exemplification of one preferred embodiment thereof. Other variations are possible. Accordingly, the scope of the invention should be determined not by the embodiments illustrated, but by the appended claims and their legal equivalents.

I claim:

1. A hydroxyapatite filament comprised of a mixture of hydroxyapatite and hydroxyapatite whiskers.

2. The hydroxyapatite filament of claim 1 having a tensile strength greater than 140 MPa.

3. The hydroxyapatite filament of claim 1 having a tensile modulus greater than 40 GPa.

4. The hydroxyapatite filament of claim 1 whose largest lateral dimension is greater than 5 microns and whose length is greater than 1 millimeter.

* * * * *